United States Patent
Wakefield et al.

(10) Patent No.: US 6,879,860 B2
(45) Date of Patent: Apr. 12, 2005

(54) COCHLEAR IMPLANT MAP OPTIMIZATION WITH USE OF A GENETIC ALGORITHM

(76) Inventors: Gregory Howard Wakefield, 3016 Cedarbrook Rd., Ann Arbor, MI (US) 48105; Christopher van den Honert, 15061 E. Aberdeen Ave., Centennial, CO (US) 80016

( * ) Notice: Subject to any disclaimer, the term of this patent is extended or adjusted under 35 U.S.C. 154(b) by 124 days.

(21) Appl. No.: 10/385,880

(22) Filed: Mar. 11, 2003

(65) Prior Publication Data

US 2004/0181266 A1 Sep. 16, 2004

(51) Int. Cl.[7] .................................................. A61N 1/08
(52) U.S. Cl. .......................................... 607/57; 600/559
(58) Field of Search .............................. 607/55–57, 59; 600/559; 381/23.1, 312, 314; 128/920, 924, 925; 73/585

(56) References Cited

U.S. PATENT DOCUMENTS 4,953,112 A * 8/1990 Widin et al. .................... 703/6
6,157,861 A * 12/2000 Faltys et al. .................. 607/57

OTHER PUBLICATIONS

Forrest, Stephanie, "Genetic Algorithms: Principles of Natural Selection Applied to Computation", Science, Aug. 13, 1993, vol. 281(5123), pp 872–878.

Takagi, Hideyuki, "Interactive Evolutionary Computation: Fusion of the Capabillities of EC Optimization and Human Evaluation", Proceedings of the IEEE, Sep. 2001, vol. 89, No. 9, pp. 1275–1296.

\* cited by examiner

*Primary Examiner*—Kennedy Schaetzle (57) ABSTRACT

A method for fitting a cochlear implant to a patient. A genetic algorithm operates to generate successive generations of multiple groups of values for a parameter subset, and patient feedback during execution of the genetic algorithm determines the multiple groups of subset values in successive generations. In each generation, half of the groups of values for the parameter subset are selected and used to determine the groups of values for the next generation. Values for the parameters not included in the subset are selected by any traditional method that does not use a genetic algorithm. In one illustrative embodiment of the invention, there are only three parameters in the subset that are selected by a genetic algorithm—parameters relating to rate, number of channels and filtering characteristics.

106 Claims, 7 Drawing Sheets

REPRODUCTION: OFFSPRING INHERITS SOME OF ITS GENES FROM EACH PARENT (HALF AND HALF EXAMPLE):

GENERATION 5
EVOLUTION SEQUENCE
FIG. 2a

GENERATION 5
SELECTION
FIG. 2b

GENERATION 5
SURVIVAL OF
THE FITTEST
FIG. 2c

PAIRS OF PARENTS
PROCREATE
FIG. 2d

GENERATION 6
OFFSPRING FORM
NEXT GENERATION
FIG. 2e

AN ORGANISM IS A MAP DEFINED BY A
SET OF 8 BINARY GENES:

FIG. 3a

REPRODUCTION: OFFSPRING INHERITS SOME OF ITS GENES
FROM EACH PARENT (HALF AND HALF EXAMPLE):

| BIT STRING | MAP PARAMETERS | | | | |
|---|---|---|---|---|---|
| | RATE | # OF MAXIMA | # OF ELECTRODES | COMPRESSION (Q) | AUDIO FILTERING |
| 00000000 | 250 | 4 | 22 | 20 | FLAT |
| 00000001 | 250 | 6 | 22 | 20 | FLAT |
| 00000010 | 250 | 8 | 22 | 20 | FLAT |
| 00000011 | 720 | 6 | 22 | 20 | FLAT |
| 00000100 | 1200 | 8 | 22 | 20 | FLAT |
| 00000101 | 720 | 12 | 22 | 20 | FLAT |
| 00000110 | 250 | 16 | 22 | 20 | FLAT |
| 00000111 | 250 | 16 | 22 | 20 | FLAT |
| | 119 OTHER LEGAL COMBINATIONS OF RATE, # OF MAXIMA, # OF ELECTRODES, COMPRESSION Q, AND AUDIO FILTERING | | | | |
| 01111111 | 250 | 4 | 10 | 30 | HIGH CUT |
| 10000000 | 250 | 4 | 22 | 20 | LOW CUT |
| | 126 OTHER LEGAL COMBINATIONS OF RATE, # OF MAXIMA, # OF ELECTRODES, COMPRESSION Q, AND AUDIO FILTERING | | | | |
| 11111111 | 250 | 4 | 10 | 30 | HIGH CUT + LOW CUT |

COCHLEAR IMPLANT MAP OPTIMIZATION WITH USE OF A GENETIC ALGORITHM

This invention relates to cochlear implants and more particularly to the use of a genetic algorithm in the fitting of a cochlear implant.

BACKGROUND OF THE INVENTION

A. Cochlear Implants

Modern cochlear implant prostheses provide a wide variety of fitting options that can be customized for each individual recipient. At the highest level, one of several stimulation 'strategies' may be selected. Each strategy defines an algorithm for converting acoustic sound input into a sequence of electrical stimuli applied to electrodes within the cochlea. Examples of strategies currently in clinical use are the SPEAK, ACE, CIS and SAS strategies.

Within any given strategy a great many parameters and parameter values may be set to tailor the encoding and stimulation for an individual patient. Examples of parameters and parameter values that may be selected for a strategy are the number of frequency bands (channels) represented, the intracochlear and/or extracochlear electrodes associated with each channel, the pulse repetition rate for each channel, the pulse width for each channel, the number of spectral maxima periodically chosen for representation, the mapping of sound pressure to stimulus current for each channel (thresholds, comfort levels and compression curves), front end filtering of the audio from the microphone (pre-emphasis), and automatic gain control threshold, compression ratio, and attack and release times. (As used herein, the term 'parameter values' refers collectively to values of parameters, whether selectable options are programmed on or off, and in general to any choices that are made during a fitting procedure.)

The ability of a cochlear implant user to understand speech or recognize other sounds depends strongly on the strategy selection and the adjustment of parameters. It is known that no single set of parameters provides an optimal outcome for all users. Users are heterogeneous such that, in general, each user requires a different set of parameters to achieve optimal performance. Parameter values must be tailored to the individual in order to maximize speech reception or user satisfaction.

The task of the clinical professional, usually an audiologist, is to choose a et of parameters—called a 'MAP'—that will provide the best possible outcome for an individual user. Because there are hundreds or thousands of possible MAPs, it is not practical to try all of the alternatives exhaustively and to evaluate performance of each for an individual user. Nor is it possible to identify an optimal MAP by prescription based upon a limited set of measures as is, for example, the case in fitting eyeglasses or a hearing aid. Optimal fitting of cochlear implants by prescriptive testing has not proved to be consistently successful. Nor is it possible to optimize parameters one at a time, adjusting each in succession to its best value. This is because the parameters interact strongly, and often non-monotonically. For example, increasing stimulus rate may improve the outcome for one set of electrodes, but worsen it for another set.

As a result, clinicians have adopted a variety of approaches for fitting the device parameters to the patient. Some simply fit default parameters to all users. Some adopt preferred MAPs, which they believe are good, if not best, for many or most individuals. These may be based upon personal experience, published performance data, or intuition. Some clinicians evaluate a limited set of alternatives. Some attempt to adjust individual parameters based upon measured perceptual limitations and inferred relationships to fitting parameters. These approaches are time consuming, costly, and unreliable.

The fundamental problem remains that there is no known method for systematically identifying the particular MAP that achieves the best outcome for an individual patient. And this problem is exacerbated each time that manufacturers expand available parameter ranges or introduce new encoding strategies.

In the absence of a prescriptive procedure, an adaptive procedure can sometimes be employed to solve an optimization problem. An adaptive procedure steps through a sequence of solutions with the objective of converging gradually towards the best one. Traditional analytic optimization procedures use current and past measurements of performance to predict, at each iteration, parameter adjustments that will incrementally improve the outcome. But these methods generally fail when there are strong nonlinear and nonmonotonic interactions among parameters as is the case in cochlear implant fitting. They may converge toward a local maximum rather than the absolute maximum, or fail to converge at all. They may also fail when the measurements are noisy, as is often the case when measuring auditory response in humans.

Figure 1A:
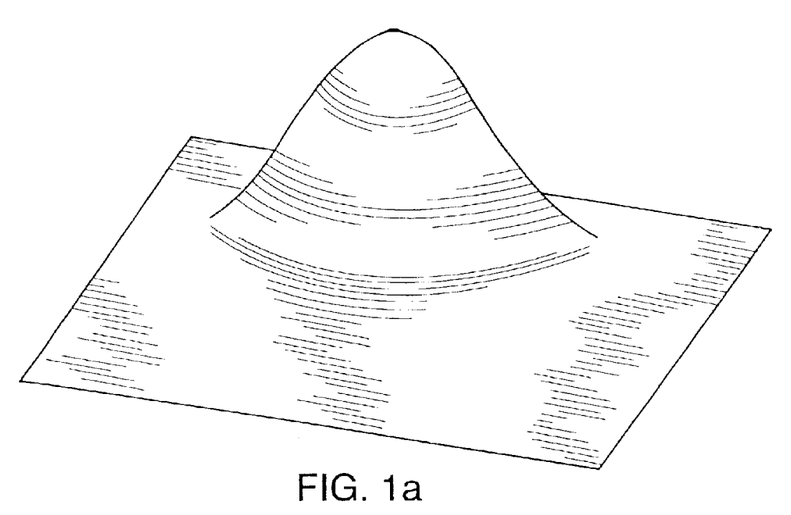
FIGS. 1A and 1B, discussed above, help explain why it has been believed that adaptive procedures in general, and a genetic algorithm in particular, could not be used to fit a cochlear implant.
Figure 1B:
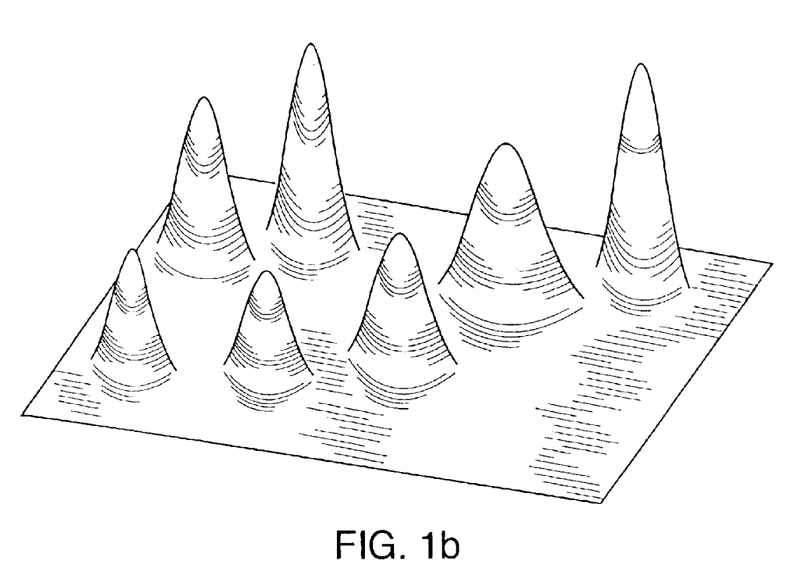

The problem referred to can be appreciated by studying FIGS. 1A and 1B. They represent a simple case in which values for only two parameters, on the X and Y axes, must be determined. The vertical (Z) axis represents the 'fitness function,' i.e. how good a result is produced by each X-Y pair of values. In FIG. 1A, the value of either variable can be optimized without radically affecting optimization of the other. There is only one 'hump' and eventually an adaptive procedure will give rise to X and Y values whose fitness function is a maximum, at the top of the hump. But in FIG. 1B, changing the value of either variable affects the optimum value of the other. Once the variable values are situated on a hump, the adaptive procedure may give rise to X and Y values whose fitness function is a local maximum (at the top of the hump), but there may be another hump, with a higher peak, that the variables never even reach. It has been believed that adaptive procedures in fitting a cochlear implant would converge toward a local maximum rather than a global maximum, and that adaptive procedures might not converge at all.

B. The Genetic Algorithm

The genetic algorithm is an adaptive procedure, based on a simple model of biological evolution, which can be used to find optimal solutions to a problem. The procedure implements 'natural selection' (survival of the fittest), 'procreation with inheritance,' and random 'mutation.' Genetic algorithms generally resist convergence on local maxima. The underlying premise is that the evolutionary process will, over multiple generations, produce an 'organism' which is optimal in the sense that it is most likely to survive and procreate.

Each iteration of the genetic algorithm procedure begins with one generation of organisms and produces a succeeding generation. This involves two steps: (1) selection—choosing a subset of organisms as potential 'parents' of the organisms ('children') of the succeeding generation; and (2) procreation—creation of 'children' from sets of potential 'parents' (usually pairs).

In genetic algorithms, selection operates on strings of binary digits stored in the computer's memory, and over time, the functionality of these strings evolves in much the same way that natural populations evolve. Genetic algorithms are capable of evolving surprisingly complex and interesting structures. These structures may represent not only solutions to problems, but also strategies for playing games, visual images, or even simple computer programs. The Darwinian theory of evolution depicts biological systems as the product of the ongoing process of natural selection. Likewise, genetic algorithms allow engineers to use a computer to evolve solutions over time, instead of designing them by hand. Because almost any method, theory, or technique can be programmed on a computer, this implies an approach to problem solving that can be, at least partially, automated by a computer.

The basic idea of a genetic algorithm is that first a population of organisms is created in a computer (typically with genes stored as binary strings in the computer's memory), and then the population is evolved with use of the principles of variation, selection, and inheritance. There are many ways of implementing this idea, but the most basic is that suggested by J. H. Holland, in Adaptation in Natural and Artificial Systems, Univ. of Michigan Press, Ann Arbor, Mich., 1975, reprinted by MIT Press, Cambridge, Mass., 1992. Each of a group of organisms in a 'generation' is assigned a fitness value by a fitness function. On the basis of these fitness values, the selection phase ranks the organisms. After selection, genetic operators are applied probabilistically; some organisms may have bits in their genes mutated from a 1 to a 0 or a 0 to a 1, and parts of different organisms' genes are then combined into new ones. The resulting population comprises the next generation and the process repeats itself.

The fitness function is the primary place in which the traditional genetic algorithm is tailored to a specific problem. Once all organisms in the population of a particular generation have been evaluated, their fitnesses are used as the basis for selection. Selection is implemented by eliminating low-fitness individuals from the population, and inheritance is often implemented by making multiple copies of high-fitness individuals. Genetic operators such as mutation (flipping individual bits) and crossover or inheritance (exchanging sub-strings of two organisms to obtain two offspring) are applied probabilistically to the selected individuals to produce new organisms. By replacing members of the old generation with such new organisms, new generations are produced either synchronously, so that the old generation is completely replaced, or asynchronously, so that the new and old members of the generation overlap. The genetic operators have been shown to generate new organisms that, on average, are better than the average fitness of their parents. Therefore, when this cycle of evaluation, selection, and genetic operations is iterated for many generations, the overall fitness of the population generally improves, on average, and the organisms in the population represent improved 'solutions' to whatever problem was posed in the fitness function.

Selection can be performed in any of several ways. It can arbitrarily eliminate the least fit 50% of the population and make one copy of all the remaining organisms, it can replicate organisms in direct proportion to their fitness, or it can scale the fitnesses in any of several ways and replicate organisms in direct proportion to their scaled values (a more typical method). Likewise, the crossover operator can pass on both offspring to the new generation, or it can arbitrarily choose one to be passed on. These and other variations of the basic algorithm are well known in the art.

C. The Genetic Algorithm and Cochlear Implants

The genetic algorithm has been applied to hearing aids, the art closest to that of cochlear implants. The fitness function in this type of case is not based on application of a formula. Rather, the user provides feedback in the form of accepting or rejecting organisms in a population, where each organism is a set of parameter values, or the user ranks the organisms and thus affects which organisms populate the next generation. This variation of the genetic algorithm, involving feedback or interactivity, is discussed in a review article by H. Takagi, Interactive Evolutionary Computation: Fusion of the Capabilities of EC Optimization and Human Evaluation, Proceedings of the IEEE, Vol. 89, No. 9, September 2002., pp. 1275–1296.

The genetic algorithm has not been applied, however, to cochlear implants. Even though there is an extensive literature on the genetic algorithm, including applications with a human observer in the loop and one specifically fitting hearing aids, the task of fitting a cochlear implant is so daunting that most workers did not believe the genetic algorithm could be adapted to cochlear implants. The hearing aid prior art obliged the listener to scale (assign a numerical value to) each member of the population. Even experienced cochlear implant users cannot reliably scale the quality of the percept. The sound sensation varies so much across fittings, and can be disparate in so many ways, that numerical scaling is essentially impossible. So all prior art using scaling in the evaluation function is impractical for the cochlear implant task. This is even more of a problem with naive (newly implanted) users, to whom all of the percepts are foreign. Even ranking without scaling would be difficult for new users.

Moreover, the complexity of the fitting (the number of parameters to be adjusted) would demand too many bits in each population member. With many bits, the number of members per population must be high, and that would swamp the user with choices to evaluate. This is both impractical in time spent, and impossible for the listener who cannot reasonably compare many simultaneous options.

SUMMARY OF THE INVENTION

In the invention, a cochlear implant is at least partially fitted to a patient by executing a genetic algorithm to select values for a subset of all the parameters for which values must be selected to fit the implant. The genetic algorithm operates to generate successive generations of multiple groups of values for this parameter subset, and patient feedback during execution of the genetic algorithm determines the multiple groups of subset values in successive generations. Selection is thus based on the subjective listening judgment of the patient during execution of the genetic algorithm. In each generation, substantially less than all (e.g., half) of the groups of values for the parameter subset are selected and used to determine a larger number of groups of values for the next generation (e.g., twice as large, if it is desired that all generations be of the same size). Values for the parameters outside the subset are selected by any traditional method that does not use a genetic algorithm. In fact, what makes use of a genetic algorithm practical in a cochlear application is that most of the parameters are not selected by using a genetic algorithm. In one illustrative embodiment of the invention, there are only three parameters in the subset that are selected by a genetic algorithm— parameters relating to rate, number of channels and filtering characteristics. These are the characteristics that many clinicians feel are the most important in the fitting process.

The patient feedback involves selecting preferred groups of parameter subset values in one generation ('survivors') from which the groups of parameter subset values in the next generation are determined, but preferably groups of subset values are not ranked. They are selected for use in deriving the next generation or they are not selected, but the patient does not rank groups of subset values from best to worst. With eight groups per generation, for example, the patient simply has to choose the four he likes best.

Preferably, the values of the subset of parameters are represented by a binary string of 6–12 bits, with 8 bits being used in the illustrative embodiments of the invention. It is also best that there be 6–12 groups of parameter subset values ('children') in each generation, with 8 groups being used in the illustrative embodiments of the invention.

In the examples to be discussed in detail below, the values of the subset of parameters are represented by a string of bits. The string of bits may be divided into separate substrings each of which represents the value of a respective parameter. Alternatively, each different valued string may simply identify a respective subset of parameter values without specific bit positions in the string being associated with particular parameters. It is even possible to have some of the bits in the string divided into separate sub-strings each of which represents the value of a respective parameter, and the others of the bits in the string identifying respective pre-selected parameter subset values.

The parts of strings of bits that are combined to form an offspring may be cut from parent strings at positions that separate parameter values (if separate sub-strings represent the values of respective parameters). The strings may be cut at positions that do not vary from generation to generation, or they may be cut at positions that do vary, even randomly, from generation to generation. In the illustrative embodiment of the invention, the genetic algorithm is executed a fixed number of times, e.g., 15, to generate a fixed number of successive generations of multiple groups of values for the parameter subset, and a final group of values for the parameter subset is selected from the groups in the final generation. However, alternative stopping criteria are possible. Examples of alternative criteria are ones based upon a measure of homogeneity within generations, or a measure of consistency of the listener's judgments. In addition, a record may be made of any group of values for the parameter subset that the patient identifies as satisfactory in any generation, and a final group of values for the parameter subset may be selected from the groups in the final generation and those previously identified by the patient.

As in traditional applications of genetic algorithms, successive generations of multiple groups of values for the parameter subset are determined in part by mutations. Preferably, in each generation the probability of each bit in a string of bits mutating is fixed for all bits, e.g., at between 1% and 10%, with 3% being preferred. (It is possible for the clinician or even the patient to vary the mutation rate as the algorithm is executed. Similarly, depending on the progress of the algorithm, it is possible for the algorithm to change its own mutation rate.)

The multiple groups of values for the parameter subset that are used in the first generation of the execution of the genetic algorithm may be based on predetermined clinician judgment. Alternatively, the multiple groups of values for the parameter subset that are used in the first generation of the execution of the genetic algorithm may be random.

To conclude this summary of the invention, broadly speaking the invention is a method of at least partially fitting a cochlear implant to a patient that comprises the steps of forming a set of digit sequences, each sequence representing a respective set of parameter values for the implant. The implant is tested on the patient using the parameter values represented in the sequences and the sequences that provide superior performance are selected. Parts of the selected sequences are then combined to form new sequences. The testing, selecting and combining steps are then iteratively repeated to derive a final sequence for use in fitting the implant.

BRIEF DESCRIPTION OF THE DRAWINGS

Further objects, features and advantages of the invention will become apparent upon consideration of the following detailed description in conjunction with the drawing, in which.

DETAILED DESCRIPTION OF THE PREFERRED EMBODIMENTS

There will first be described some of the terms used in connection with genetic algorithms and, in some cases, how these terms are applied to genetic algorithms for fitting cochlear implants in accordance with the invention.

Figure 3A:
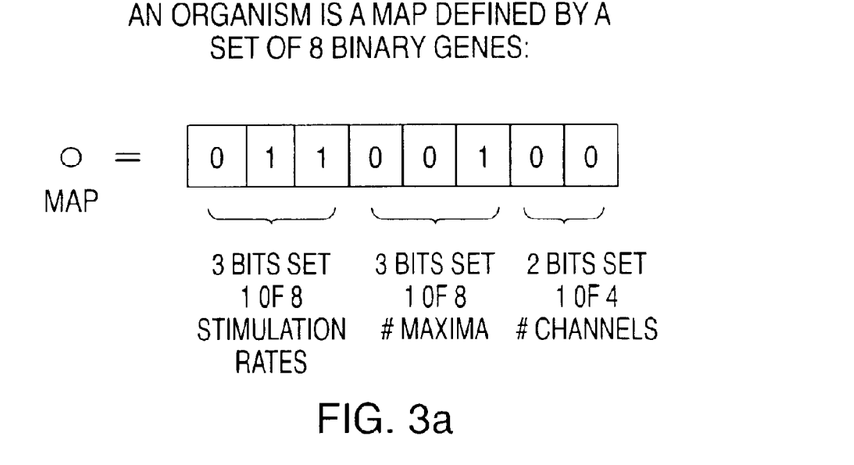
FIG. 3A depicts how specific bits in any bit string can represent values of respective parameters in the first illustrative embodiment of the invention.

An 'organism' is entirely defined by a set of $N_b$ 'genes' (bits). The number of possible unique organisms is $2^{Nb}$. In the invention, the organism to be optimized is a cochlear MAP (values for a set of parameters). In the example of FIG. 3A, $N_b$ is 8 so a MAP is defined by a gene set of 8 bits, and there are 256 possible MAPs. Three of the bits are used to select 1 of 8 stimulus rates (the rate, in Hz or pulses/second, at which high-energy channels are selected and stimulus pulses are delivered to groups of N electrodes), three bits select 1 of 8 spectral maxima counts (the number N of electrodes periodically selected to be stimulated, representing the N frequency bands with the highest energy at the time), and the remaining two bits select 1 of 4 channel counts (the number M of channels, or frequency bands, used to represent the sound spectrum; periodically, electrodes whose corresponding channels have the highest energy are selected to be stimulated). Other MAP parameters are assumed to be constant or derived from one of the three represented parameters; they are fitted using traditional methods. (If additional parameters are to be optimized using a genetic algorithm, then $N_b$ may be increased.) The set of 8 bits is a binary number, but the string has no numerical significance.

A 'generation' comprises a set of organisms. Generally, the number of organisms $N_g$ is constant from generation to generation. In the illustrative embodiment of the invention, $N_g=8$. An initial generation must be specified. In the illustrative embodiment of the invention, the initial generation comprises a selection of 8 different MAPs, which span the parametric ranges. These MAPs can be completely random. Alternatively, some or all MAPs of the initial generation may be the preferences of clinicians, or may be selected from the results of a previous execution of the method.

Some 'fitness function' is used to evaluate each of the organisms in each generation. The fitness function identifies those organisms that will survive to become parents and procreate. Generally, the number of survivors is constant from generation to generation. In the illustrative embodiment of the invention, half of the organisms survive. Also, in the illustrative embodiment of the invention the fitness function is a subjective listening test performed by the user. He or she listens to speech presented through each of the 8 MAPs in a generation, and selects the four MAPs that produce the best intelligibility. Alternatively, the fitness of a MAP may be determined entirely, or in part, from measures not involving judgment by the listener, such as cortical or brainstem evoked potentials measured from the listener, the listener's ability to repeat a speech token, the quality of a the listener's speech while listening to his own speech with the MAP, results of an objective speech reception test, or expert knowledge about known beneficial parameter combinations. 'Reproduction' involves three separate operations: pairing of parents, inheritance, and mutation. In the illustrative embodiment of the invention, a round-robin algorithm is used to identify four pairs of parents in each generation. (This simply means that each parent is paired with each of two others.) Each pair produces two children, resulting in a new generation of 8 children. Each child inherits some of its 'genes' from each parent. The boundary within the 8-bit set, which separates genes from each parent, is referred to as the cut point. Several different cut points are possible, as will be described. Finally, after reproduction, each gene is subject to random inversion (mutation) with some small probability, typically 1–10%, and 3% in the preferred embodiment of the invention.

Figure 2A:
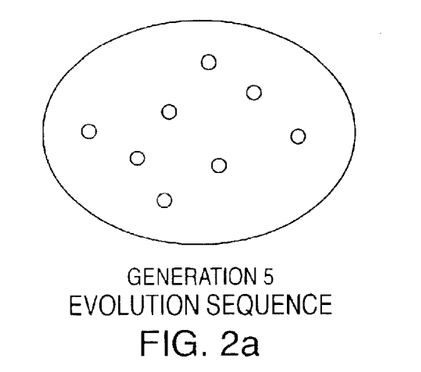
FIGS. 2A–2E depict successive steps in the performance of the genetic algorithm for a specific generation (generation 5 in the example) in accordance with the principles of the invention.
Figure 2B:
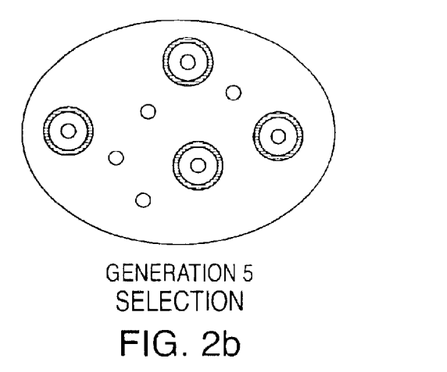
Figure 2C:
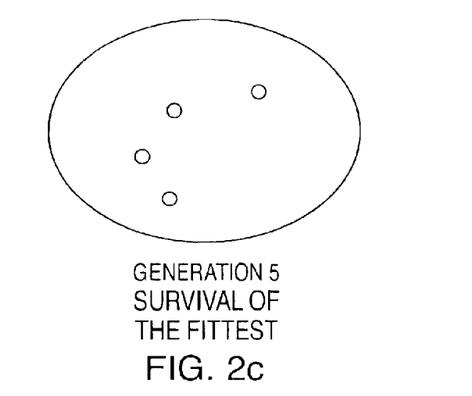
Figure 2D:
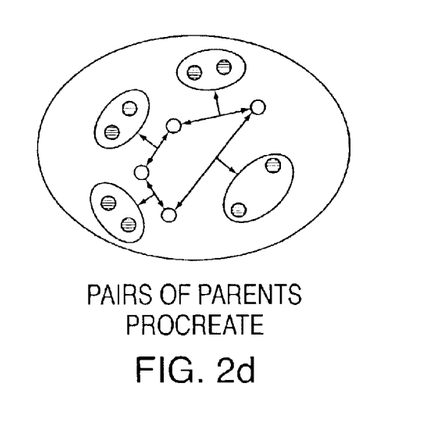
Figure 2E:
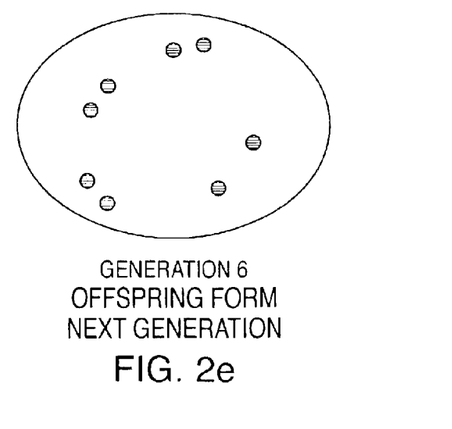

Referring to FIG. 2A, the drawing depicts some arbitrary generation in an overall sequence (generation 5 in the example) that has evolved to contain 8 organisms or individuals. A 'fitness function' rejects four of these (circled organisms are those being rejected), as shown in FIG. 2B, with FIG. 2C showing the survivors. The survivors are then paired, as shown in FIG. 2D, with each survivor mating with two others. Each pair produces two children. The 8 children make up generation 6, as shown in FIG. 2E.

Figure 3B:
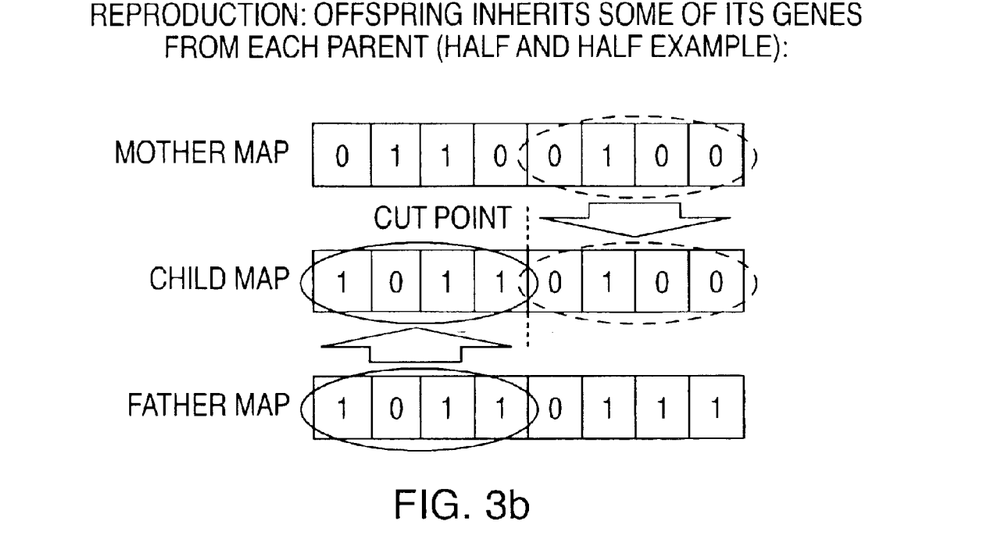
FIG. 3B illustrates how two 'parents' reproduce.

FIG. 3A shows how an organism (the leftmost circle in FIG. 3A, corresponding to the circles in FIGS. 2A–2E) is a MAP defined by a set of 8 binary genes. In this case, 3 bits set or represent 1 of 8 stimulation rates, 3 bits set 1 of 8 maxima counts, and 2 bits set 1 of 4 channel counts. For each of the 8 stimulation rates, a corresponding set of threshold (T) and comfort (C) levels, one for each electrode, is also selected. Ts and Cs are determined by clinician measurement at the corresponding rate, or by inference, using a mathematical loudness model, from Ts and Cs measured at a single standard rate. FIG. 3B shows how an offspring inherits some genes from each parent. The cut point in this case is in the middle of each bit string. The child MAP includes the first 4 bits of the Mother MAP and the last 4 bits of the Father MAP.

Figure 3C:
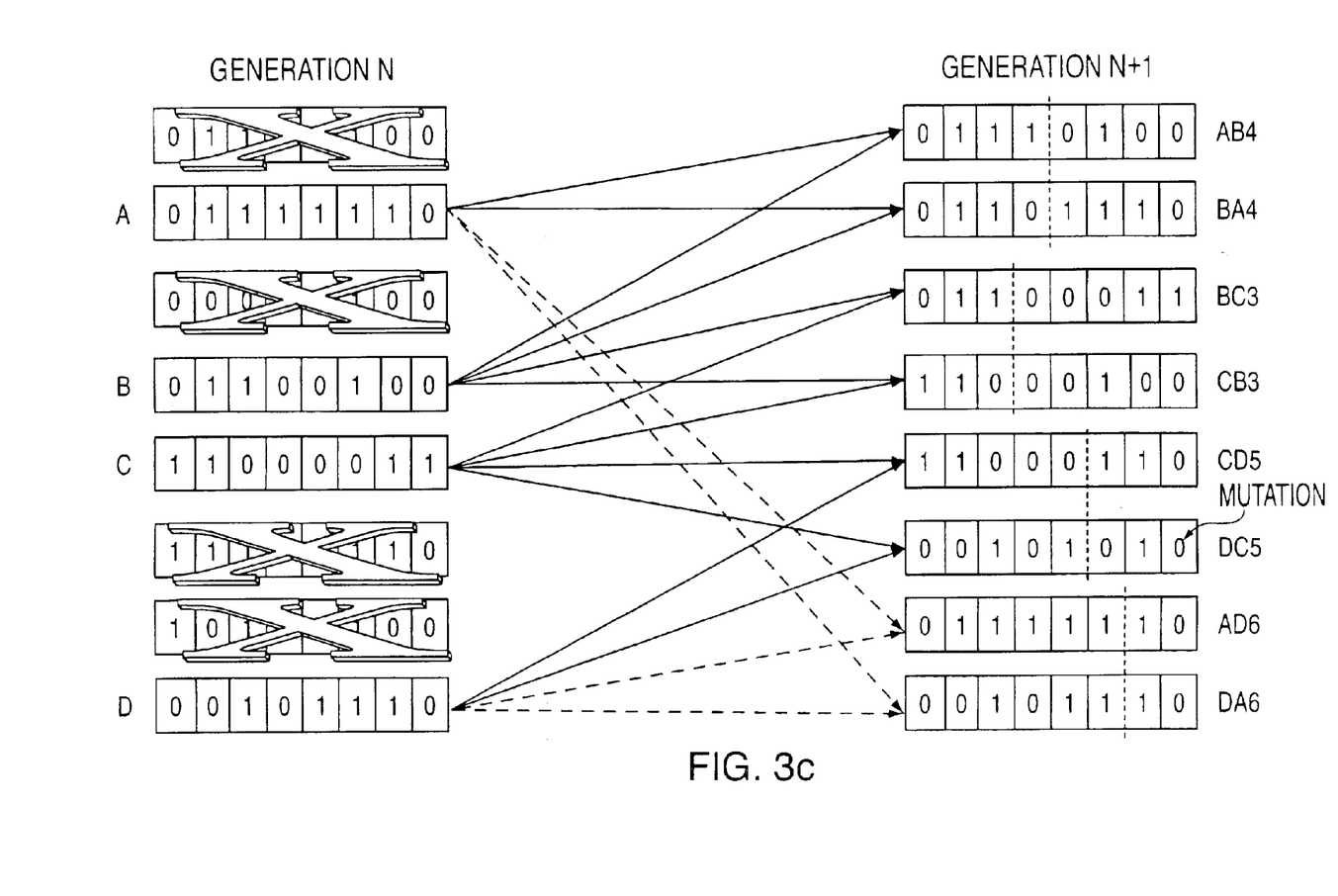
FIG. 3C shows how only 4 of the 8 organisms in generation N survive, and how they then reproduce and give rise to 8 organisms in generation N+1.

The sequence of selection and reproduction is illustrated in FIG. 3C. The large crosses on the left identify non-survivors of the original generation. Four pairs of surviving parents (at the tails of the arrows) each produce two children. Each parent has two mates. The cut points which govern inheritance of genes from each parent are illustrated by the vertical dotted lines through each child on the right. Genes to the left of the cut point come from one parent, and genes to the right come from the other parent. In the illustrated example, the cut point is allowed to vary randomly across pairings. Finally, one bit has been inverted (mutated) in the sixth child of the new generation. (Each child is identified by a notation such as CD5. The first letter represents the organism in generation N that contributes leftmost bits to the child in generation N+1, the second letter represents the organism that contributes rightmost bits, and the numeral represents the position of the cuts.)

The process is allowed to iterate until some stopping criterion is met. One simple approach is to stop after a predetermined number of generations. At this point the user would be equipped with one or more of the surviving MAPs for regular use.

In the examples thus far, a MAP is defined by choice of stimulation rate, number of channels, and number of maxima. A MAP is completely defined by selection of these three parameters. (An actual MAP will include other parameters as well (T and C levels, pulse width, etc.) but these are assumed to be constant, or derived from represented parameters, for all of the MAPS available for selection by the algorithm.) The 8 bits that represent a unique MAP give rise to 256 possible different bit strings that represent 256 unique MAPs. Three alternative methods for representation are possible.

Lookup Table of Maps

Figure 4:
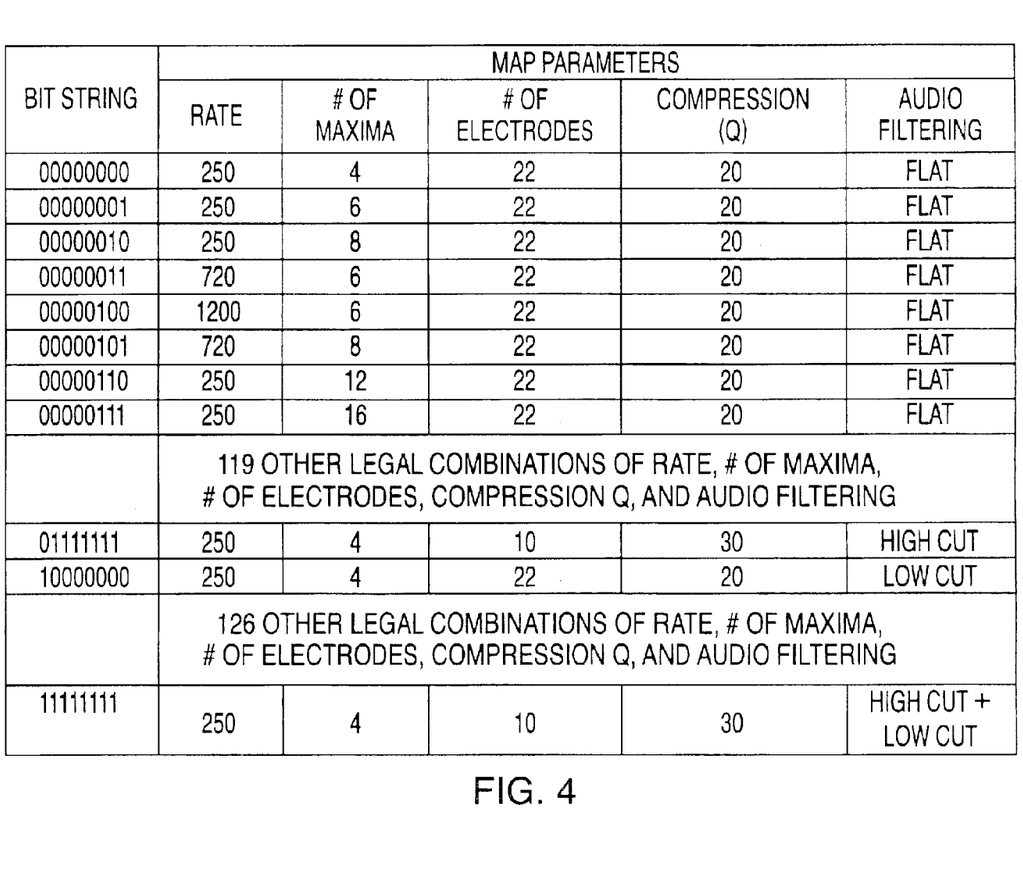
FIGS. 4–6 depict three other illustrative embodiments of the invention and show the three different ways in which a bit string can represent parameter values.

With this method, illustrated in FIG. 4, 256 predetermined maps are chosen. Each may represent any arbitrary legal combination of parameters. For example, 256 different combinations thought to be useful by expert clinicians could be selected. The only constraint is that each combination be legal and unique, i.e., no two maps may represent the same combination of parameters. A lookup table associates each of the 256 possible bit strings with one of the 256 available MAPs. Therefore, when a bit string is specified, it uniquely represents a single MAP. With this method, each parameter can have any legal value in each MAP. For example, each of the 256 possible MAPs might have a different rate. In the embodiment illustrated in FIG. 4, five parameters are varied within the set of 256 MAPs. Various, but not all, combinations of the following parameters are constructed within the set of 256 possible maps. (1) Stimulation rate (one of 250, 720, 1200, 1800, or 2400 Hz); (2) number of electrodes used (either 10 or 22); (3) number of maxima per stimulus frame (one of 4, 6, 8, 10, 12, 16, or 20); (4) steepness of output compression (known as the "Q" factor for an ACE or SPEAK map—either 20 or 30); and (5) combination of input audio filtering options (flat, high cut, low cut, or high and low cut). None of these parameters is individually represented by any particular substring within the 8-bits.

Parameter-Specific Fields

Figure 5:
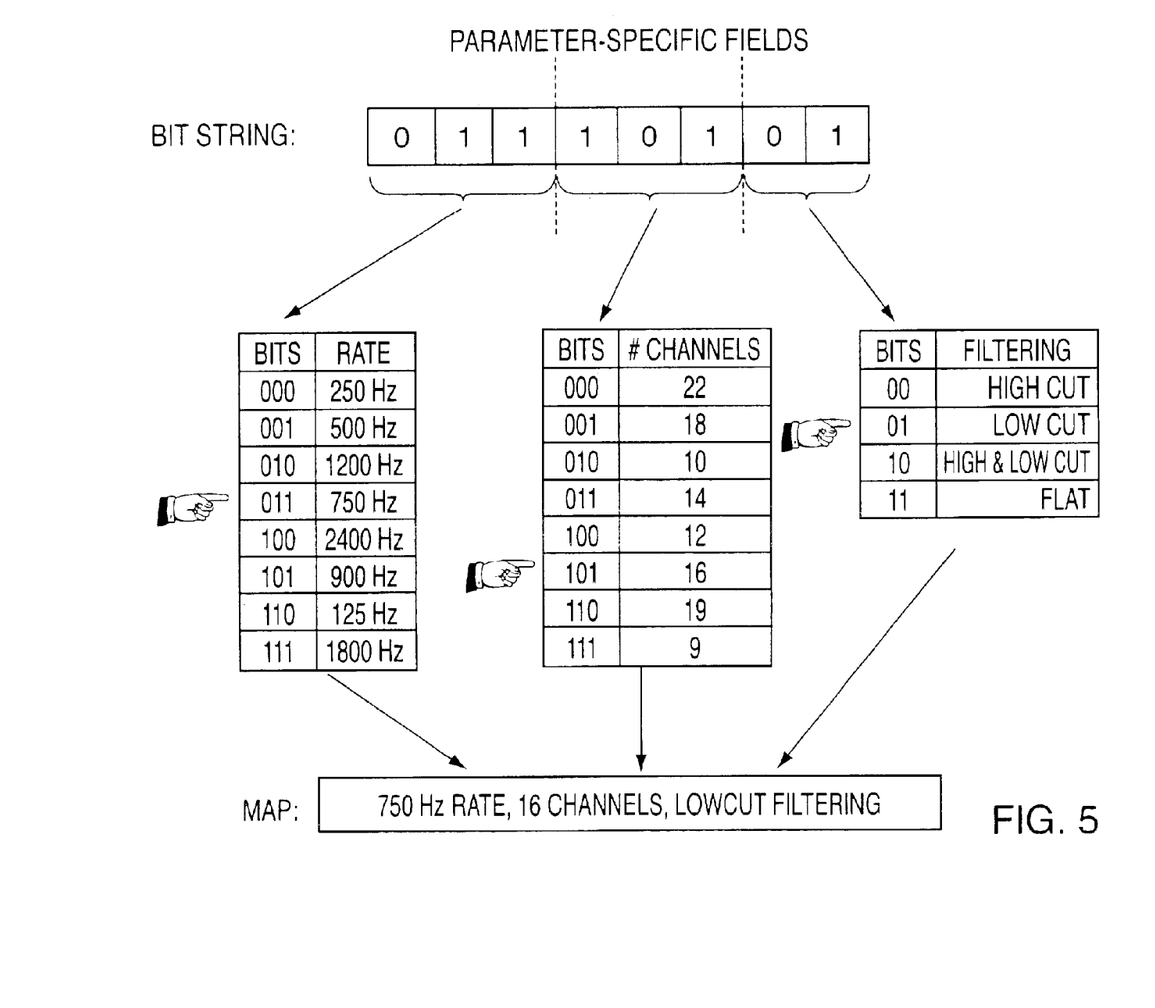

With this method, shown in FIG. 5, the bit string is broken down into sub-strings or fields. The substring in each field is then used to select a particular parameter for the MAP. In the example of FIG. 5, one 3-bit sub-string selects one of 8 possible rates for the MAP. A second 3-bit sub-string selects one of 8 possible channel counts, and a third 2-bit sub-string selects one of 4 possible filtering options. In this example, each sub-string is contiguous. However, this is not necessary, because there is no significance to the order of the bits in the bit string.

With this method, the available options for any given parameter are fixed by the number of bits in the corresponding sub-string. In the example of FIG. 5, only 8 different rates are available. No MAP can be defined with a rate of 792 Hz, for example, because this rate is not one of the 8 available alternatives.

Combination of Parameter Fields and Lookup

Figure 6:
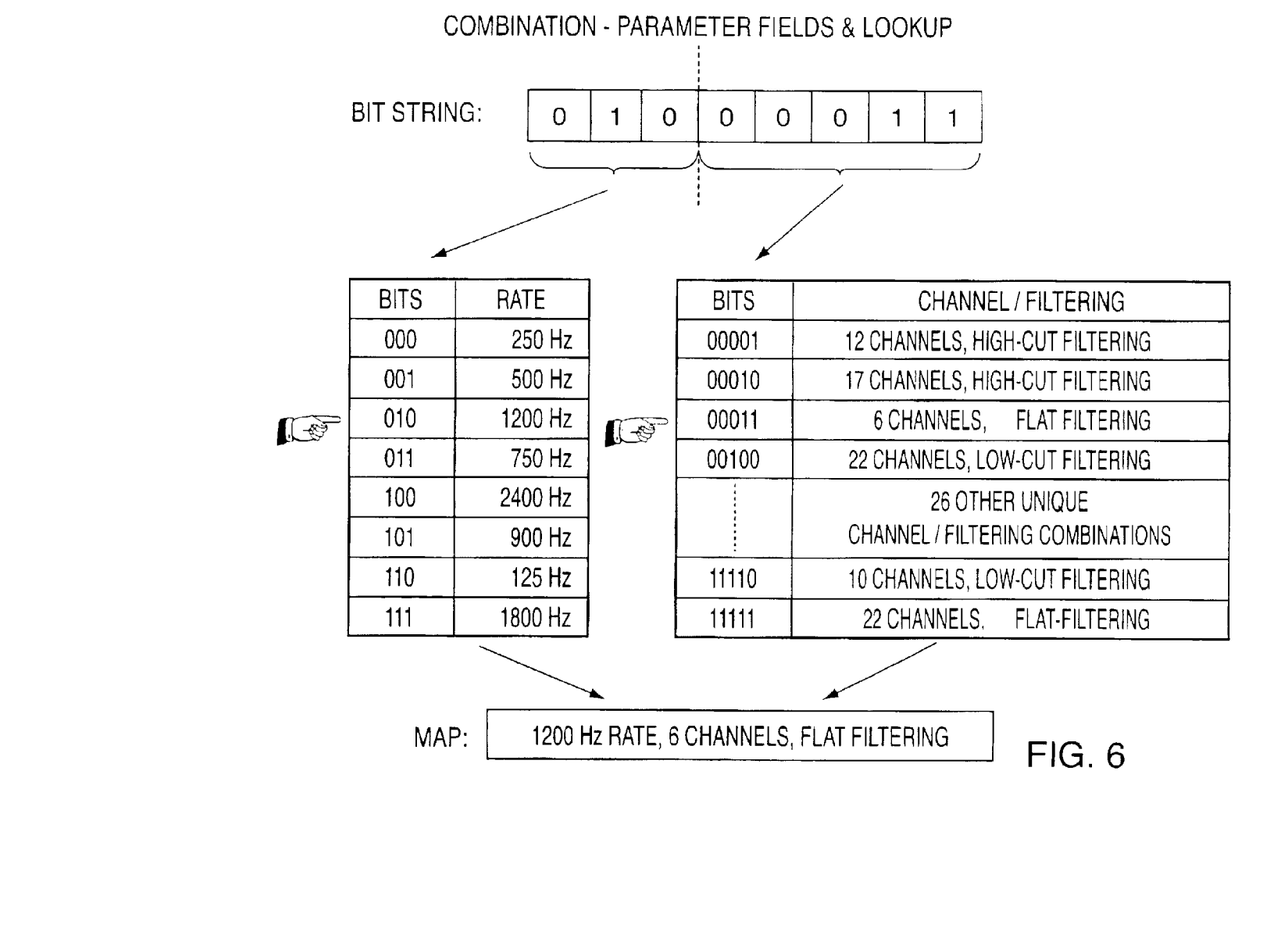

This method, depicted in FIG. 6, is a combination of the previous two methods. One or more sub-strings are defined to select corresponding parameters as in FIG. 5. The remaining bits are used to choose from a table of arbitrary combinations of the remaining parameters. In the example of FIG. 6, one 3-bit sub-string selects one of 8 possible rates. The remaining 5 bits are used to choose, from a lookup table, one of 32 arbitrary combinations of channel count and filtering. As with the first method, each of the 32 arbitrary combinations must be legal and unique.

The Fitting Process

Following initialization of the procedure, the fitting process iterates through generations of designs until the stopping criterion is met. The implant patient may save particularly good designs during each iteration in a "gallery", and may return to the gallery at any time to observe any of the saved designs. The implant patient may also terminate the fitting process early.

The patient evaluates each of the designs in the current generation and selects the best of the current generation for updating. The bit strings associated with the selected designs of the current generation are represented as parents, using the described "round-robin" or some other technique. For each pair of parents, the described inheritance technique is applied to create a pair of children. The described mutation operator is applied to each child. The set of children that results from this sequence of operations becomes the current generation for the next iteration.

Initialization requires the selection of first generation of designs. This selection is typically performed by selecting at random from among the set of possible designs. However, pre-selected designs may be included among the first generation. These pre-selected designs may be drawn from prior runs of the fitting procedure, including designs from the implant patient's gallery or designs from the terminal run, or the designs may be drawn from ones selected by a clinician.

A genetic algorithm has several properties that make it appealing for optimization of cochlear implant fitting. It is resistant to convergence upon local maxima, it is robust and can tolerate a noisy, inconsistent, or non-linear fitness function (e.g., subjective judgments by the user), it can incorporate 'expert knowledge,' and it is easily automated. Although less than all of the following can be specified in a practical application of the invention, a complete implementation for MAP optimization might include the following:

1) The choice of $N_b$
2) The method for defining a MAP from a set of $N_b$ bits (or, more generally, a set of genes)
3) The number of MAPs per generation $N_g$
4) Initialization—the method for defining the MAPs in the initial generation
5) Fitness function—the mechanism for selecting survivors
6) Pairing operator—determines the number of parental pairs per generation, the method for selecting them, and number of children per pair (it is possible to implement a system in which children inherit genes from more than two parents)
7) Inheritance operator—the method for determining which of a child's genes come from each parent (the cut point)
8) Mutation operator—the method for randomly determining which genes of a child are inverted from their inherited state
9) Stopping criterion Generally, all of these specifications are constant across generations, but this need not necessarily be the case. There may be specific advantages to having some of these specifications vary within a single evolutionary sequence.

The details of the implementation can significantly affect the behavior and efficiency of the algorithm, particularly its speed of convergence. The fitness function need not be purely subjective, e.g., it can be based on cortical evoked potentials either alone or with subjective inputs. But if the fitness function used involves subjective comparisons by a user, it is important to limit $N_g$ because a human listener cannot reasonably compare dozens of concurrent alternatives. A subjective fitness function is also 'expensive' in terms of time, which makes rapid convergence important. In general, the number of generations required for convergence rises with the number of genes per organism ($N_b$), so it is desirable to keep $N_b$ as small as possible while still representing those MAP parameters which are most likely to influence performance.

Preferably, at each iteration the user is given the opportunity to flag MAPs to be saved for future consideration. In this way if the process 'stumbles' onto a particularly good MAP it can be saved for comparison against the eventual result of the evolution. This eliminates the risk of frustrating the user. If multiple runs are used, saved designs, or designs resulting from a first run, can be included in the initial population for a subsequent run.

Expert knowledge can be incorporated into the process in various ways. As noted above, the MAPs of the initial generation can be based upon clinical judgment. Also, specific parametric combinations known to be detrimental can be excluded from the universe of possible MAPs. Conversely, specific parametric combinations known to be beneficial can be condensed into a single 'parameter,' or occurrence of a specific value of one parameter may be used to override and dictate the value of a different parameter (e.g., any time the rate is >2400 Hz, the number of channels is limited to 10). Finally, as the population evolves, the expert may serve as an auxiliary form of input to guide the evolution in particular directions. For example, the clinician, based upon a visual representation of the evolution of the parameters, may anticipate more efficient paths to an optimal region. This expert knowledge can then be used to help steer the update mechanism in the proper direction.

The method of the invention has the advantage that it can be automated, requiring no supervision by the audiologist. It may also be repeated periodically as the recipient becomes more experienced. Separate optimizations may be performed for specific classes of input signals (e.g., speech in quiet, speech in noise, music, etc).

In principle, the recipient could perform optimizations at home using signals of his or her own choosing (e.g., a spouse's voice).

Although the invention has been described with reference to particular embodiments it is to be understood that these embodiments are merely illustrative of the application of the principles of the invention. Numerous modifications may be made therein and other arrangements may be devised without departing from the spirit and scope of the invention.

We claim:

1. A method of at least partially fitting a cochlear implant to a patient comprising the following acts:
   (a) executing a genetic algorithm to select values for a subset of all the parameters for which values must be selected to fit the implant, the genetic algorithm operating to generate successive generations of multiple groups of values for said parameter subset, and
   (b) using patient feedback during execution of the genetic algorithm to determine the multiple groups of parameter subset values in successive generations.

2. A method of at least partially fitting a cochlear implant to a patient in accordance with claim 1 further including the following act:
   (c) selecting values for the parameters not included in said subset by a method that does not use a genetic algorithm.

3. A method of at least partially fitting a cochlear implant to a patient in accordance with claim 2 wherein said patient feedback involves selecting, without ranking, preferred groups of parameter subset values in one generation from which the groups of parameter subset values in the next generation are determined.

4. A method of at least partially fitting a cochlear implant to a patient in accordance with claim 3 wherein the values of said subset of parameters are represented by a binary string of 6–12 bits.

5. A method of at least partially fitting a cochlear implant to a patient in accordance with claim 3 wherein there are 6–12 groups of parameter subset values in each generation.

6. A method of at least partially fitting a cochlear implant to a patient in accordance with claim 3 wherein the values of said subset of parameters are represented by a string of bits, with different sub-strings of bits in said string representing values of respective parameters.

7. A method of at least partially fitting a cochlear implant to a patient in accordance with claim 6 wherein the parameters in said subset are related to rate, number of channels and filtering characteristics.

8. A method of at least partially fitting a cochlear implant to a patient in accordance with claim 3 wherein the values of said subset of parameters are represented by a string of bits, each different valued string identifying a predetermined group of parameter values.

9. A method of at least partially fitting a cochlear implant to a patient in accordance with claim 8 wherein the parameters in said subset are related to rate, number of channels and filtering characteristics.

10. A method of at least partially fitting a cochlear implant to a patient in accordance with claim 3 wherein the values of said subset of parameters are represented by a string of bits, some of the bits in said string being divided into separate sub-strings each of which represents the value of a respective parameter, and the others of the bits in said string identifying a predetermined group of parameter values.

11. A method of at least partially fitting a cochlear implant to a patient comprising the steps of:
    (a) executing a genetic algorithm to select values for a subset of all the parameters for which values must be selected to fit the implant, the genetic algorithm operating to generate successive generations of multiple groups of values for said parameter subset, and
    (b) based on the subjective listening judgment of the patient during execution of the genetic algorithm, selecting substantially less than all of the groups of values for said parameter subset in each generation and determining from them a larger number of groups of values for the next generation.

12. A method of at least partially fitting a cochlear implant to a patient in accordance with claim 11 wherein N groups of values for said parameter subset are determined for each generation, and N/2 of said groups are selected in each generation for the determination of the N groups in the next generation.

13. A method of at least partially fitting a cochlear implant to a patient in accordance with claim 12 wherein each of the N/2 of said groups selected in each generation is paired with each of two others of said groups, with each pair being used for the determination of two groups in the next generation.

14. A method of at least partially fitting a cochlear implant to a patient in accordance with claim 13 wherein the patient selects N/2 groups in each generation and the selected groups are then used to determine the groups in the next generation independent of any rankings among the N/2 groups.

15. A method of at least partially fitting a cochlear implant to a patient in accordance with claim 11 wherein the selected groups in each generation are used to determine the groups in the next generation independent of any rankings among the selected groups.

16. A method of at least partially fitting a cochlear implant to a patient in accordance with claim 11 wherein there are 6–12 groups of parameter subset values in each generation.

17. A method of at least partially fitting a cochlear implant to a patient in accordance with claim 11 wherein the values of said subset of parameters are represented by a string of bits, the string of bits being divided into separate sub-strings each of which represents the value of a respective parameter.

18. A method of at least partially fitting a cochlear implant to a patient in accordance with claim 17 wherein the string of bits for representing each group of values for the next generation is determined by combining parts of two different strings of bits that represent groups of values for the current generation.

19. A method of at least partially fitting a cochlear implant to a patient in accordance with claim 18 wherein the parts of strings of bits that are combined are cut from strings at positions that separate parameter values.

20. A method of at least partially fitting a cochlear implant to a patient in accordance with claim 17 wherein the parts of strings of bits that are combined are cut from strings at positions that do not vary from generation to generation.

21. A method of at least partially fitting a cochlear implant to a patient in accordance with claim 17 wherein the parts of strings of bits that are combined are cut from strings at positions that vary from generation to generation.

22. A method of at least partially fitting a cochlear implant to a patient in accordance with claim 11 wherein the genetic algorithm is executed a fixed number of times to generate a fixed number of successive generations of multiple groups of values for said parameter subset, and a final group of values for the parameter subset is selected from the groups in the final generation.

23. A method of at least partially fitting a cochlear implant to a patient in accordance with claim 11 wherein a record is made of any group of values for said parameter subset that the patient identifies as satisfactory in any generation, and a final group of values for the parameter subset is selected from the groups in the final generation and those previously identified by the patient.

24. A method of at least partially fitting a cochlear implant to a patient in accordance with claim 11 wherein the parameters in each subset are related to rate, number of channels and filtering characteristics.

25. A method of at least partially fitting a cochlear implant to a patient in accordance with claim 11 wherein successive generations of multiple groups of values for said parameter subset are determined in part by mutations.

26. A method of at least partially fitting a cochlear implant to a patient in accordance with claim 11 wherein the values for said subset of parameters are represented by a string of bits, each string of bits being associated with a predetermined set of parameter values.

27. A method of at least partially fitting a cochlear implant to a patient in accordance with claim 11 wherein the values for said subset of parameters are represented by a string of bits, and successive generations of multiple groups of values for said parameter subset are determined in part by mutations.

28. A method of at least partially fitting a cochlear implant to a patient in accordance with claim 27 wherein in each generation the probability of each bit in a string of bits mutating is fixed for all bits.

29. A method of at least partially fitting a cochlear implant to a patient in accordance with claim 27 wherein, in any generation in which mutations are allowed, the probability of each bit in a string of bits mutating is between 2% and 4%.

30. A method of at least partially fitting a cochlear implant to a patient in accordance with claim 11 wherein the multiple groups of values for said parameter subset that are used in the first generation of the execution of the genetic algorithm are based on predetermined clinician judgment.

31. A method of at least partially fitting a cochlear implant to a patient in accordance with claim 11 wherein the multiple groups of values for said parameter subset that are used in the first generation of the execution of the genetic algorithm is random.

32. A method of at least partially fitting a cochlear implant to a patient in accordance with claim 11 wherein the multiple groups of values for said parameter subset that are used in the first generation of the execution of the genetic algorithm is based at least partially on the results of an earlier execution of the genetic algorithm.

33. A method of at least partially fitting a cochlear implant to a patient in accordance with claim 32 wherein the parameters in said subset are related to rate, number of channels and filtering characteristics.

34. A method of at least partially fitting a cochlear implant to a patient in accordance with claim 11 wherein the values of said subset of parameters are represented by a string of bits, some of the bits in said string being divided into separate sub-strings each of which represents the value of a respective parameter, and the others of the bits in said string identifying a predetermined group of parameter values.

35. A method of at least partially fitting a cochlear implant to a patient in accordance with claim 11 further including the step of:
(c) selecting values for the parameters not included in said subset by a method that does not use a genetic algorithm.

36. A method of at least partially fitting a cochlear implant to a patient in accordance with claim 35 wherein said patient selects preferred groups of parameter subset values in one generation from which the groups of parameter subset values in the next generation are determined.

37. A method of at least partially fitting a cochlear implant to a patient in accordance with claim 36 wherein said patient selects preferred groups of parameter subset values by classifying them as selected or unselected without ranking them.

38. A method of at least partially fitting a cochlear implant to a patient comprising the steps of:
(a) executing a genetic algorithm to select values for at least a subset of all the parameters for which values must be selected to fit the implant, the genetic algorithm operating to generate successive generations of multiple groups of values for said parameter subset, and
(b) using patient feedback during execution of the genetic algorithm to select a specified number of groups of values to survive in each generation from which multiple groups of values for said parameter subset are determined for the next generation.

39. A method of at least partially fitting a cochlear implant to a patient in accordance with claim 38 wherein N groups of values for said parameter subset are determined for each generation, and N/2 of said groups survive in each generation from which the N groups in the next generation are determined.

40. A method of at least partially fitting a cochlear implant to a patient in accordance with claim 39 wherein each of the N/2 of said groups that survive in each generation is paired with each of two others of said groups, with each pair being used for the determination of two groups in the next generation.

41. A method of at least partially fitting a cochlear implant to a patient in accordance with claim 38 wherein the patient selects N/2 groups in each generation and the selected groups are then used to determine the groups in the next generation independent of any rankings among the N/2 groups.

42. A method of at least partially fitting a cochlear implant to a patient in accordance with claim 38 wherein the surviving groups in each generation are used to determine the groups in the next generation independent of any rankings among the surviving groups.

43. A method of at least partially fitting a cochlear implant to a patient in accordance with claim 38 wherein there are 6–12 groups of parameter subset values in each generation.

44. A method of at least partially fitting a cochlear implant to a patient in accordance with claim 38 wherein the values of said subset of parameters are represented by a string of bits, the string of bits being divided into separate sub-strings each of which represents the value of a respective parameter.

45. A method of at least partially fitting a cochlear implant to a patient in accordance with claim 44 wherein the string of bits for representing each group of values for the next generation is determined by combining parts of two different strings of bits that represent surviving groups of values for the current generation.

46. A method of at least partially fitting a cochlear implant to a patient in accordance with claim 45 wherein the parts of strings of bits that are combined are cut from strings at positions that separate parameter values.

47. A method of at least partially fitting a cochlear implant to a patient in accordance with claim 45 wherein the parts of strings of bits that are combined are cut from strings at positions that do not vary from generation to generation.

48. A method of at least partially fitting a cochlear implant to a patient in accordance with claim 45 wherein the parts of strings of bits that are combined are cut from strings at positions that vary from generation to generation.

49. A method of at least partially fitting a cochlear implant to a patient in accordance with claim 38 wherein the genetic algorithm is executed a fixed number of times to generate a fixed number of successive generations of multiple groups of values for said parameter subset, and a final group of values for the parameter subset is selected from the groups in the final generation.

50. A method of at least partially fitting a cochlear implant to a patient in accordance with claim 38 wherein a record is made of any group of values for said parameter subset that the patient identifies as satisfactory in any generation, and a final group of values for the parameter subset is selected from the groups in the final generation and those previously identified by the patient.

51. A method of at least partially fitting a cochlear implant to a patient in accordance with claim 38 wherein the parameters in each subset are related to rate, number of channels and filtering characteristics.

52. A method of at least partially fitting a cochlear implant to a patient in accordance with claim 38 wherein successive generations of multiple groups of values for said parameter subset are determined in part by mutations.

53. A method of at least partially fitting a cochlear implant to a patient in accordance with claim 38 wherein the values for said subset of parameters are represented by a string of bits, each string of bits being associated with a predetermined set of parameter values.

54. A method of at least partially fitting a cochlear implant to a patient in accordance with claim 38 wherein the values for said subset of parameters are represented by a string of bits, and successive generations of multiple groups of values for said parameter subset are determined in part by mutations.

55. A method of at least partially fitting a cochlear implant to a patient in accordance with claim 54 wherein in each generation the probability of each bit in a string of bits mutating is the same for all bits.

56. A method of at least partially fitting a cochlear implant to a patient in accordance with claim 54 wherein, in any generation in which mutations are allowed, the probability of each bit in a string of bits mutating is between 2% and 4%.

57. A method of at least partially fitting a cochlear implant to a patient in accordance with claim 38 wherein the multiple groups of values for said parameter subset that are used in the first generation of the execution of the genetic algorithm is based on predetermined clinician judgment.

58. A method of at least partially fitting a cochlear implant to a patient in accordance with claim 38 wherein the multiple groups of values for said parameter subset that are used in the first generation of the execution of the genetic algorithm is random.

59. A method of at least partially fitting a cochlear implant to a patient in accordance with claim 38 wherein the values of said subset of parameters are represented by a string of bits, with different sub-strings of bits in said string representing values of respective parameters.

60. A method of at least partially fitting a cochlear implant to a patient in accordance with claim 59 wherein the parameters in said subset are related to rate, number of channels and filtering characteristics.

61. A method of at least partially fitting a cochlear implant to a patient in accordance with claim 38 wherein the values of said subset of parameters are represented by a string of bits, some of the bits in said string being divided into separate sub-strings each of which represents the value of a respective parameter, and the others of the bits in said string identifying a predetermined group of parameter values.

62. A method of at least partially fitting a cochlear implant to a patient in accordance with claim 38 further including the step of:
(c) selecting values for the parameters not included in said subset by a method that does not use a genetic algorithm.

63. A method of at least partially fitting a cochlear implant to a patient in accordance with claim 62 wherein said patient selects preferred groups of parameter subset values in one generation from which the groups of parameter subset values in the next generation are determined.

64. A method of at least partially fitting a cochlear implant to a patient in accordance with claim 63 wherein said patient selects preferred groups of parameter subset values by classifying them as selected and unselected without ranking them.

65. A method of at least partially fitting a cochlear implant to a patient comprising the steps of forming a set of digit sequences, each sequence being divided into groups which represent the values of respective parameters for the implant; testing the implant on the patient using the values represented in said sequences and selecting the sequences that provide superior performance; combining parts of selected sequences to form new sequences; and iteratively repeating the testing, selecting and combining steps to derive a sequence for use in finally fitting the implant.

66. A method of at least partially fitting a cochlear implant to a patient in accordance with claim 65 wherein sequences are selected based on patient feedback without ranking sequences.

67. A method of at least partially fitting a cochlear implant to a patient in accordance with claim 65 wherein said sequences comprise 6–12 binary digits.

68. A method of at least partially fitting a cochlear implant to a patient in accordance with claim 67 wherein there are 6–12 sequences in each iteration.

69. A method of at least partially fitting a cochlear implant to a patient in accordance with claim 65 wherein there are 6–12 sequences in each iteration.

70. A method of at least partially fitting a cochlear implant to a patient in accordance with claim 65 wherein the parameters whose values are represented in said sequences are related to rate, number of channels and filtering characteristics.

71. A method of at least partially fitting a cochlear implant to a patient in accordance with claim 65 wherein the values of respective parameters for the implant in a sequence are represented by a string of bits, the string of bits being divided into separate sub-strings each of which represents the value of a respective parameter.

72. A method of at least partially fitting a cochlear implant to a patient in accordance with claim 71 wherein the string of bits for representing a value in a sequence is determined by combining parts of two different strings of bits each of which represents one or more parameter values.

73. A method of at least partially fitting a cochlear implant to a patient in accordance with claim 72 wherein the parts of strings of bits that are combined are cut from strings at positions that separate parameter values.

74. A method of at least partially fitting a cochlear implant to a patient in accordance with claim 73 wherein the parts of strings of bits that are combined are cut from strings at positions that do not vary from generation to generation.

75. A method of at least partially fitting a cochlear implant to a patient in accordance with claim 73 wherein the parts of strings of bits that are combined are cut from strings at positions that vary from generation to generation.

76. A method of at least partially fitting a cochlear implant to a patient in accordance with claim 65 wherein a record is made of any sequence that is identified as being satisfactory, and a final sequence is selected from the last set of sequences that is used in testing and those previously identified as being satisfactory.

77. A method of at least partially fitting a cochlear implant to a patient in accordance with claim 65 wherein the parameters represented in each sequence are related to rate, number of channels and filtering characteristics.

78. A method of at least partially fitting a cochlear implant to a patient in accordance with claim 65 wherein new sequences are determined in part by randomly changing digits.

79. A method of at least partially fitting a cochlear implant to a patient in accordance with claim 65 wherein the values of respective parameters for the implant in a sequence are represented by a string of bits, each string of bits being associated with a predetermined set of parameter values.

80. A method of at least partially fitting a cochlear implant to a patient in accordance with claim 65 wherein the values of respective parameters for the implant in a sequence are represented by a string of bits, and successive sequences are determined in part by random changes.

81. A method of at least partially fitting a cochlear implant to a patient in accordance with claim 80 wherein the probability of each bit in a string of bits being randomly changed is fixed for all bits.

82. A method of at least partially fitting a cochlear implant to a patient in accordance with claim 81 wherein the probability of each bit in a string of bits being randomly changed is between 2% and 4%.

83. A method of at least partially fitting a cochlear implant to a patient in accordance with claim 65 wherein the sequences that are first used are based on predetermined clinician judgment.

84. A method of at least partially fitting a cochlear implant to a patient in accordance with claim 65 wherein the sequences that are first used are random.

85. A method of at least partially fitting a cochlear implant to a patient in accordance with claim 65 wherein the values of respective parameters for the implant are represented in a sequence by a string of bits, with different sub-strings of bits in said string representing values of respective parameters.

86. A method of at least partially fitting a cochlear implant to a patient in accordance with claim 85 wherein said parameters are related to rate, number of channels and filtering characteristics.

87. A method of at least partially fitting a cochlear implant to a patient in accordance with claim 65 wherein the values of respective parameters for the implant are represented in a sequence by a string of bits, some of the bits in said string being divided into separate sub-strings each of which represents the value of a respective parameter, and the others of the bits in said string identifying a predetermined group of parameter values.

88. A method of at least partially fitting a cochlear implant to a patient in accordance with claim 65 wherein said patient selects preferred groups of sequences from which parts are combined to form new sequences.

89. A method of at least partially fitting a cochlear implant to a patient in accordance with claim 88 wherein said patient selects preferred groups of sequences by classifying them as selected or unselected without ranking them.

90. A method of at least partially fitting a cochlear implant to a patient in accordance with claim 65 wherein sequences are selected based at least in part on patient feedback.

91. A method of at least partially fitting a cochlear implant to a patient comprising:
   (a) selecting values for at least a subset of all the parameters for which values must be selected to fit the implant by generating successive generations of multiple groups of values for said parameter subset, and
   (b) for each generation using patient feedback to select a specified number of groups of values from which multiple groups of values for said parameter subset are determined for the next generation.

92. A method of at least partially fitting a cochlear implant to a patient in accordance with claim 91 wherein groups of values in each generation are used to determine the groups of values in the next generation independent of any rankings among the groups in said each generation.

93. A method of at least partially fitting a cochlear implant to a patient in accordance with claim 91 wherein there are 6–12 groups of parameter subset values in each generation.

94. A method of at least partially fitting a cochlear implant to a patient in accordance with claim 91 wherein the values of said subset of parameters are represented by a string of bits, and the string of bits for representing each group of values for the next generation is determined by combining parts of two different strings of bits that represent groups of values for the current generation.

95. A method of at least partially fitting a cochlear implant to a patient in accordance with claim 91 wherein multiple groups of values for said parameter subset are selected for a fixed number of successive generations, and a final group of values for the parameter subset is selected from the groups in the final generation.

96. A method of at least partially fitting a cochlear implant to a patient in accordance with claim 91 wherein a record is made of any group of values for said parameter subset that the patient identifies as satisfactory in any generation, and a final group of values for the parameter subset is selected from the groups in the final generation and those previously identified by the patient.

97. A method of at least partially fitting a cochlear implant to a patient in accordance with claim 91 wherein the parameters in each subset are related to stimulation rate, number of electrodes used, number of maxima per stimulus frame, steepness of output compression, and combination of input audio filtering options.

98. A method of at least partially fitting a cochlear implant to a patient in accordance with claim 91 wherein successive generations of multiple groups of values for said parameter subset are determined in part by mutations.

99. A method of at least partially fitting a cochlear implant to a patient in accordance with claim 91 wherein the values for said subset of parameters are represented by a string of bits, and successive generations of multiple groups of values for said parameter subset are determined in part by mutations.

100. A method of at least partially fitting a cochlear implant to a patient in accordance with claim 99 wherein in each generation the probability of each bit in a string of bits mutating is the same for all bits.

101. A method of at least partially fitting a cochlear implant to a patient in accordance with claim 99 wherein, in any generation in which mutations are allowed, the probability of each bit in a string of bits mutating is between 2% and 4%.

102. A method of at least partially fitting a cochlear implant to a patient in accordance with claim 91 wherein the multiple groups of values for said parameter subset that are used in the first generation are based on predetermined clinician judgment.

103. A method of at least partially fitting a cochlear implant to a patient in accordance with claim 91 wherein the multiple groups of values for said parameter subset that are used in the first generation are random.

104. A method of at least partially fitting a cochlear implant to a patient in accordance with claim 91 wherein the multiple groups of values for said parameter subset that are used in the first generation are based on the results of a previous use of the method on the same patient.

105. A method of at least partially fitting a cochlear implant to a patient in accordance with claim 91 wherein said patient selects preferred groups of parameter subset values in one generation from which the groups of parameter subset values in the next generation are determined.

106. A method of at least partially fitting a cochlear implant to a patient in accordance with claim 105 wherein said patient selects preferred groups of parameter subset values by classifying them as selected and unselected without ranking them.

* * * * *